(12) United States Patent
Knopp et al.

(10) Patent No.: US 7,110,109 B2
(45) Date of Patent: Sep. 19, 2006

(54) RAMAN SPECTROSCOPY SYSTEM AND METHOD AND SPECIMEN HOLDER THEREFOR

(75) Inventors: Kevin J. Knopp, Newburyport, MA (US); Daryoosh Vakhshoori, Cambridge, MA (US)

(73) Assignee: Ahura Corporation, Wilmington, MA (US)

( * ) Notice: Subject to any disclaimer, the term of this patent is extended or adjusted under 35 U.S.C. 154(b) by 3 days.

(21) Appl. No.: 10/826,706

(22) Filed: Apr. 16, 2004

(65) Prior Publication Data

US 2004/0263843 A1 Dec. 30, 2004

Related U.S. Application Data

(60) Provisional application No. 60/463,967, filed on Apr. 18, 2003, provisional application No. 60/517,811, filed on Nov. 6, 2003.

(51) Int. Cl.
*G01J 3/44* (2006.01)
*G01N 21/03* (2006.01)
*G01N 21/65* (2006.01)

(52) U.S. Cl. .................................... 356/301; 356/246

(58) Field of Classification Search ............... 356/301, 356/246
See application file for complete search history.

(56) References Cited

U.S. PATENT DOCUMENTS 3,849,654 A * 11/1974 Malvin .................. 250/363.01

FOREIGN PATENT DOCUMENTS

WO WO 02/101365 A1 * 12/2002

* cited by examiner

*Primary Examiner*—F. L. Evans
(74) *Attorney, Agent, or Firm*—Pandiscio & Pandiscio

(57) ABSTRACT

A Raman spectroscopy system includes a laser source for providing a laser beam, and an optical probe assembly including a photonic crystal fiber light guide for receiving the laser beam from the laser source and for directing the laser beam toward a specimen of selected material, a lens for receiving the laser beam in the light guide and directing the beam onto the specimen and for receiving reflected light from the specimen and directing the reflected light back through the fiber light guide, and a dichroic beam splitter for directing a portion of the reflected beam out of the optical probe assembly. The system further includes an optical spectrum analyzer for receiving the portion of the reflected beam and for exhibiting a Raman signature of the specimen.

21 Claims, 10 Drawing Sheets

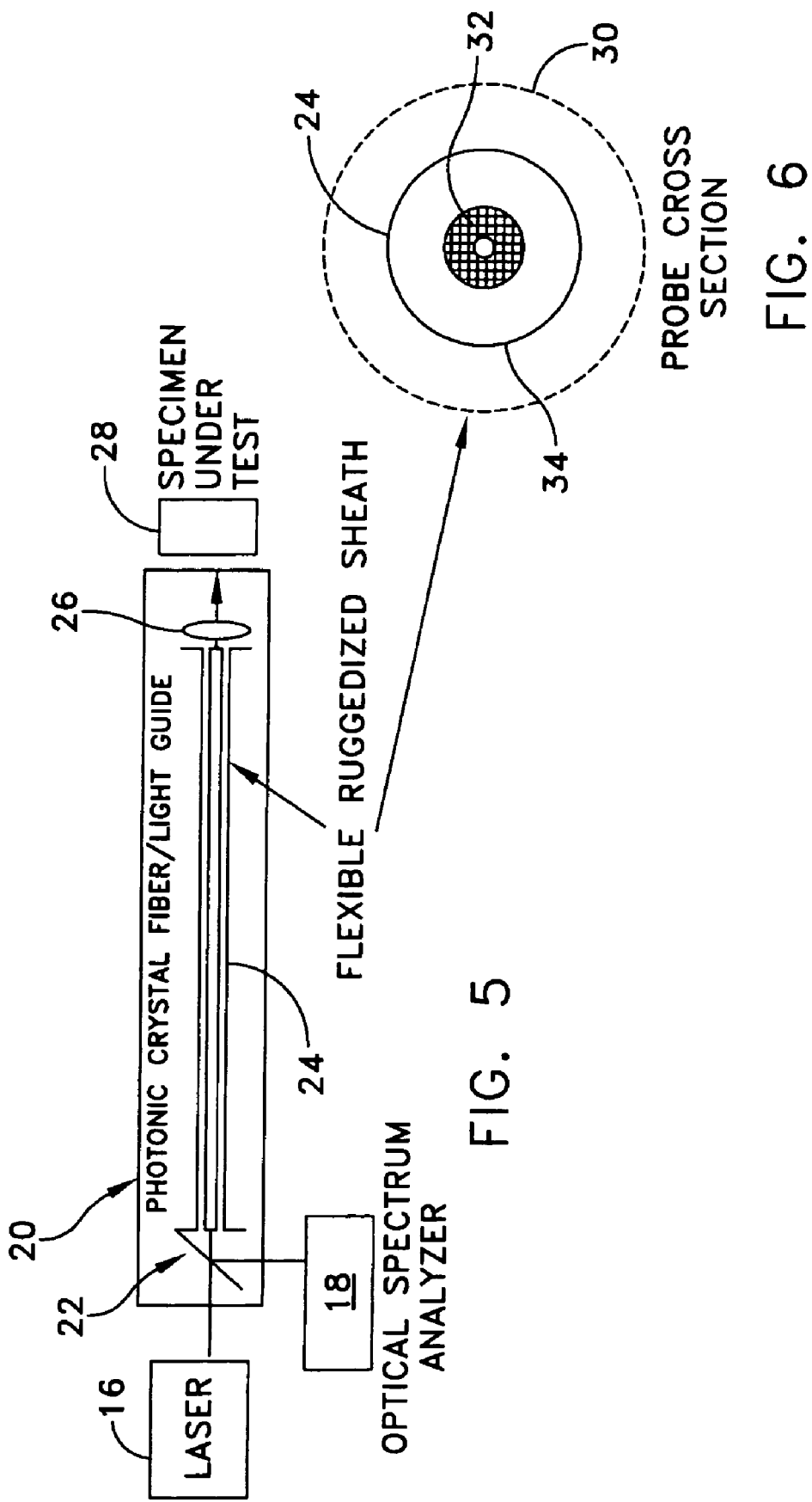

RAMAN SPECTROSCOPY SYSTEM AND METHOD AND SPECIMEN HOLDER THEREFOR

REFERENCE TO PENDING PRIOR PATENT APPLICATIONS

This patent application claims benefit of:

(1) pending prior U.S. Provisional Patent Application Ser. No. 60/463,967, filed Apr. 18, 2003 by Kevin J. Knopp et al. for SAMPLE VIAL FOR RAMAN SPECTROSCOPY WHICH ENABLES IMPROVED SPECIMEN SELECTIVITY; and (2) pending prior U.S. Provisional Patent Application Ser. No. 60/517,811, filed Nov. 6, 2003 by Kevin J. Knopp et al. for OPTICAL PROBE WITH LOW RAMAN CROSS SECTION.

The two above-identified patent applications are hereby incorporated herein by reference.

BACKGROUND OF THE INVENTION

1. Field of the Invention

This invention relates to Raman spectroscopy and is directed more particularly to a Raman spectroscopy system and method including an improved optical probe assembly, and an improved specimen holder for retaining a specimen for examination by a Raman spectroscopy system.

2. Description of the Prior Art

Raman spectroscopy is based upon the Raman effect which may be described as the scattering of light from a gas, liquid or solid with a shift in wavelength from that of the usually monochromatic incident radiation.

When a transparent medium is irradiated with an intense source of monochromatic light, and the scattered radiation is examined spectroscopically, not only is light of the exciting frequency, $n0$, observed (Rayleigh scattering), but also some weaker bands of shifted frequency are detected (FIG. 1). Moreover, while most of the shifted bands are of lower frequency $n0-ni$, there are some at higher frequency, $n0+ni$. By analogy to fluorescence spectrometry, the former are called Stokes bands 10 and the latter anti-Stokes bands 12. The Stokes and anti-Stokes bands 10, 12 are equally displaced about a Rayleigh band 14; however, the intensity of the anti-Stokes bands 12 is much weaker than the Stokes bands 10 and they are seldom observed.

If the polarizability of a molecule changes as it rotates or vibrates, incident radiation of frequency $n0$, according to classical theory, should produce scattered radiation, the most intense part of which has unchanged frequency. This is referred to as Rayleigh scattering.

In addition, there typically are Stokes and anti-Stokes lines 10, 12 of much lesser intensity and of frequencies $n0+/-ni$, respectively, where $ni$ is a molecular frequency of rotation or vibration. The anti-Stokes lines 12 are always many times less intense than the Stokes lines 10. This fact is satisfactorily explained by the quantum mechanical theory of the Raman effect.

The vibrational Raman effect is especially useful in studying the structure of the polyatomic molecule. If such a molecule contains N atoms it can be shown that there will be $3N-6$ fundamental vibrational modes of motion only ($3N-5$ if the molecule is a linear one). Those which are accompanied by a change in electric moment can be observed experimentally in the infrared. The remaining ones, if occurring with a change in polarizability, are observable in the Raman effect. Thus, both kinds of spectroscopic measurements are usually required in a complete study of a given molecule.

Like infrared spectrometry, Raman spectrometry is a method of determining modes of molecular motion, especially the vibrations, and their use in analysis is based on the specificity of such vibrations. The methods are predominantly applicable to the qualitative and quantitative analysis of covalently bonded molecules, rather than to ionic structures. Nevertheless, they can give information about the lattice structure of ionic molecules in the crystalline state and about the internal covalent structure of complex ions and the ligand structure of coordination compounds both in the solid state and in solution.

Both the Raman and the infrared spectrums yield a partial description of the internal vibrational motion of the molecule in terms of the normal vibrations of the constituent atoms. Neither type of spectrum alone gives a complete description of the pattern of molecular vibration, and, by analysis of the difference between the Raman and the infrared spectrum, additional information about the molecular structure can sometimes be inferred.

Physical chemists have made extremely effective use of such comparisons in the elucidation of the finer structural details of small symmetrical molecules, such as methane and benzene, but the mathematical techniques of vibrational analysis are not yet sufficiently developed to permit the extension of these differential studies to the Raman and infrared spectra of the more complex molecules that constitute the main body of both organic and inorganic chemistry.

The analytical geologist can use Raman and infrared spectra in two ways. At the purely empirical level, they provide "fingerprints" of the molecular structure and, as such, permit the qualitative analysis of individual compounds, either by direct comparison of the spectra of the known and unknown materials run consecutively, or by comparison of the spectrum of the unknown compound with catalogs of reference spectra. By comparisons among the spectra of large numbers of compounds of known structure, it has been possible to recognize, at specific positions in the spectrum, bands which can be identified as "characteristic group frequencies" associated with the presence of localized units of molecular structure in the molecule, such as methyl, carbonyl, or hydroxyl groups. Many of these group frequencies differ in the Raman and infrared spectra.

Thus, Raman spectroscopy is a viable technique for identifying and characterizing a vast array of compounds and materials. Applications of Raman spectroscopy are far reaching in both the scientific and the industrial arenas. Industrial areas of use include medical, biotechnology, pharmaceuticals, security, and geology. Recent technology advancements are enabling increasing application reach through a reduction in cost and size. Portable units (FIG. 2) are becoming available for out of lab uses in the measurement and identification of powders, pills, and liquids.

A persistent problem in the design of such systems is the delivery and collection of laser light and the Raman signature from the specimen. It is often desirable to have a flexible light guide for light delivery and collection. It is also often a requirement that such delivery and collection light guide be flexible, rugged, and compact in size.

Traditional optical fibers have been used for light delivery to the specimen. However, the high intensity of optical power and the non-linear coefficients of the optical fiber's refractive index cause the generation of a background Raman signal. As illustrated in FIG. 3, the presence of this background signal reduces the signal to noise of the Raman signature measurement if a single traditional optical fiber, as illustrated in FIG. 2, is used for both light delivery and collection. Thus, two or more light guides 24A and 24B are typically used, as shown in FIG. 4.

Raman spectroscopy works by launching from a laser source 16 a laser light of a particular wavelength, typically in the visible or near infrared, at a specimen 28 and collecting to an optical spectrum analyzer 18 light which has been Stokes shifted to longer wavelengths through vibrational mode interactions. By studying the position in energy of these shifted peaks, a signature of a particular material is obtained.

Traditional optical fibers introduce amorphous glass into the optical path. The amorphous nature of the glass fiber causes a broad Raman peak 38 (FIG. 3) which is collected and superimposed onto the Raman signature of the specimen. The result is a decrease in sensitivity and hence material selectivity.

Another persistent problem with Raman spectroscopy is the interference of the inherent Raman signature of the typical glass vial in which the specimen is contained with the Raman signature of the specimen being tested.

There is accordingly a need for a Raman spectroscopy system and method which includes an optical probe assembly which exhibits a low Raman cross section within the optical probe, thus reducing contamination of the specimen's Raman signature with any background Raman signal generated in the probe.

There is further a need for such a system in which the optical probe is compact, flexible, and rugged.

There is still further a need for a Raman spectroscopy system and method in which amorphous glass does not obstruct the optical path, with resulting improved sensitivity of the system.

There is yet further a need for a specimen holder for conducting Raman spectroscopy in which the Raman signature of the material of the container is configured to avoid interference with the Raman signature of the specimen.

SUMMARY OF THE INVENTION

Accordingly, an object of the invention is to produce a Raman spectroscopy system and method including an optical probe assembly which exhibits a low Raman cross section therein, to reduce contamination of the specimen's Raman signature with the background signal generated by the probe.

A further object of the invention is to provide a Raman spectroscopy system in which the optical probe assembly is compact, flexible, and rugged.

A still further object of the invention is to provide a specimen holder and method which eliminates the problems associated with the inherent Raman signature of the material of specimen holders.

With the above and other objects in view, a feature of the invention is the provision of a Raman spectroscopy system. The system includes a laser source for providing a laser beam, and an optical probe assembly. The probe assembly includes a photonic crystal light guide for receiving the laser beam from the laser source and for directing the laser beam toward a specimen of selected material, a lens for receiving the laser beam in the light guide and directing the beam onto the specimen, and for receiving reflected light from the specimen and directing the reflected light back through the light guide, and a dichroic beam splitter for directing a portion of the reflected beam out of the optical probe assembly. The system further includes an optical spectrum analyzer for receiving the portion of the reflected beam and for exhibiting a Raman signature of the specimen.

In accordance with a further feature of the invention, there is provided an improved holder for a specimen of material for which a Raman signature is to be generated. The holder includes a vial having a top member, a bottom member, and a wall member, at least one portion of at least one of said top member, said bottom member, and said side member comprising a single crystalline material.

In accordance with a further feature of the invention, there is provided a method for producing a Raman signature display. The method includes the steps of operating a laser source to produce a laser beam, directing the laser beam through a light guide and through a lens associated with the light guide, directing the laser beam further onto a selected specimen from which light projected thereonto is reflected back to the lens, passing the reflected light back through the light guide, dividing the reflected light in the light guide into a Raman signature portion and a second portion comprising a remainder of the reflected light, directing the signature portion of the reflected light to an optical spectrum analyzer, and operating the analyzer to provide a signature display.

In accordance with a still further feature of the invention, there is provided a method for producing a Raman signature display. The method includes the steps of placing a specimen for which a Raman signature is desired in a holder having at least one portion of one wall of a single crystalline material, operating a laser source to produce a laser beam, directing the laser beam through a light guide means and through a lens means associated with the light guide means, directing the laser beam through the holder at least one portion of one wall of the holder and onto the specimen from which light projected thereonto is reflected back though the light guide means into an optical spectrum analyzer, and operating the analyzer to provide a signature display.

In accordance with a yet further feature of the invention, there is provided a Raman spectroscopy optical probe assembly comprising a photonic crystal light guide for receiving the laser beam from the laser source and for directing the laser beam toward a specimen of selected material, and a lens for receiving the laser beam in the light guide and directing the beam onto the specimen, and for receiving reflected light from the specimen and directing the reflected light back through the fiber light guide.

The above and other features of the invention, including various novel details of construction and combinations of parts will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings:

FIG. 5 is a diagrammatic illustration of one form of spectroscopy system illustrative of an embodiment of the invention;

FIG. 6 is a sectional view of a portion of the system of FIG. 5;

DESCRIPTION OF PREFERRED EMBODIMENTS

Figure 1:
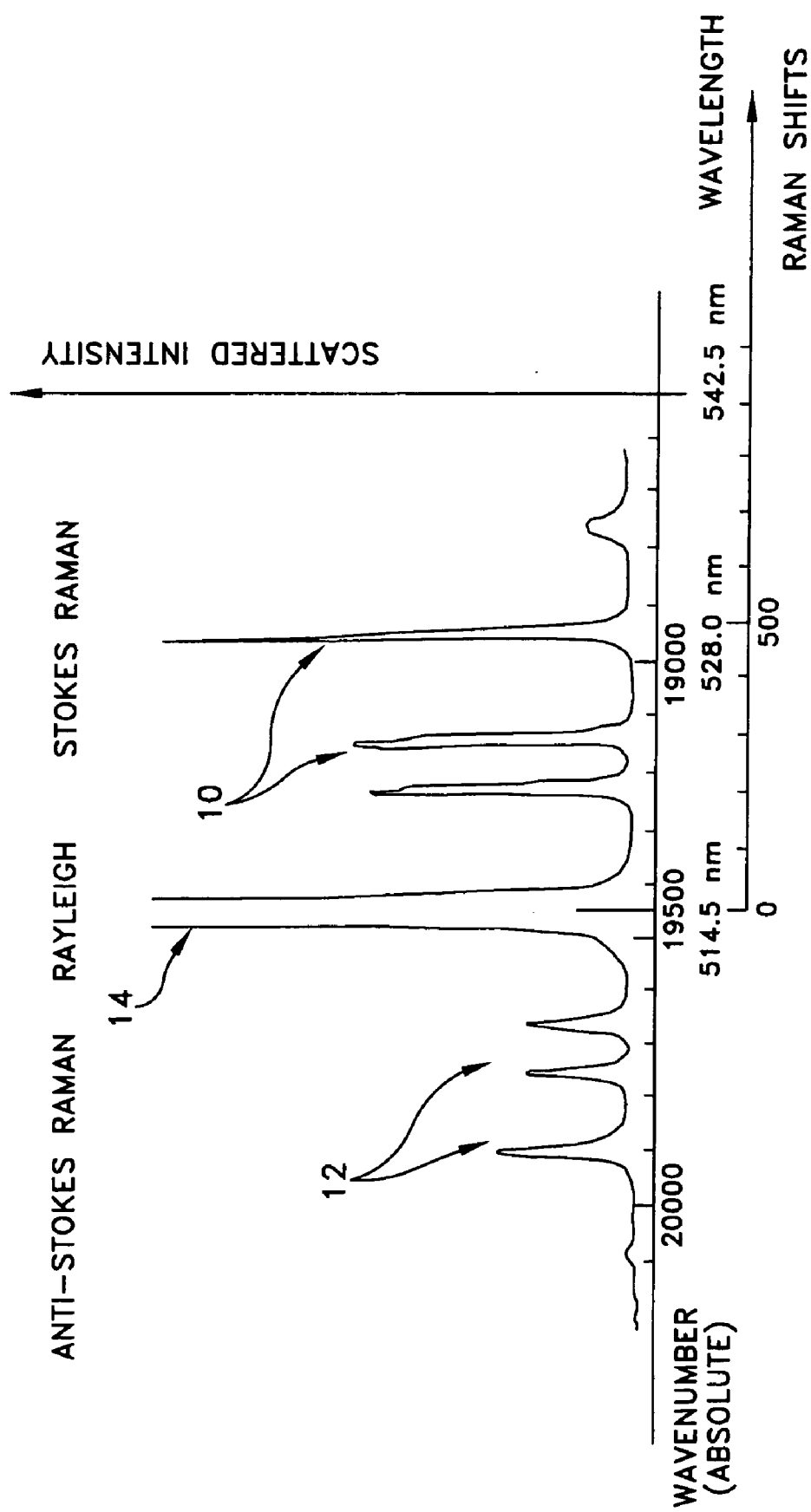
FIG. 1 is a schematic representation of a Raman signature.
Figure 2:
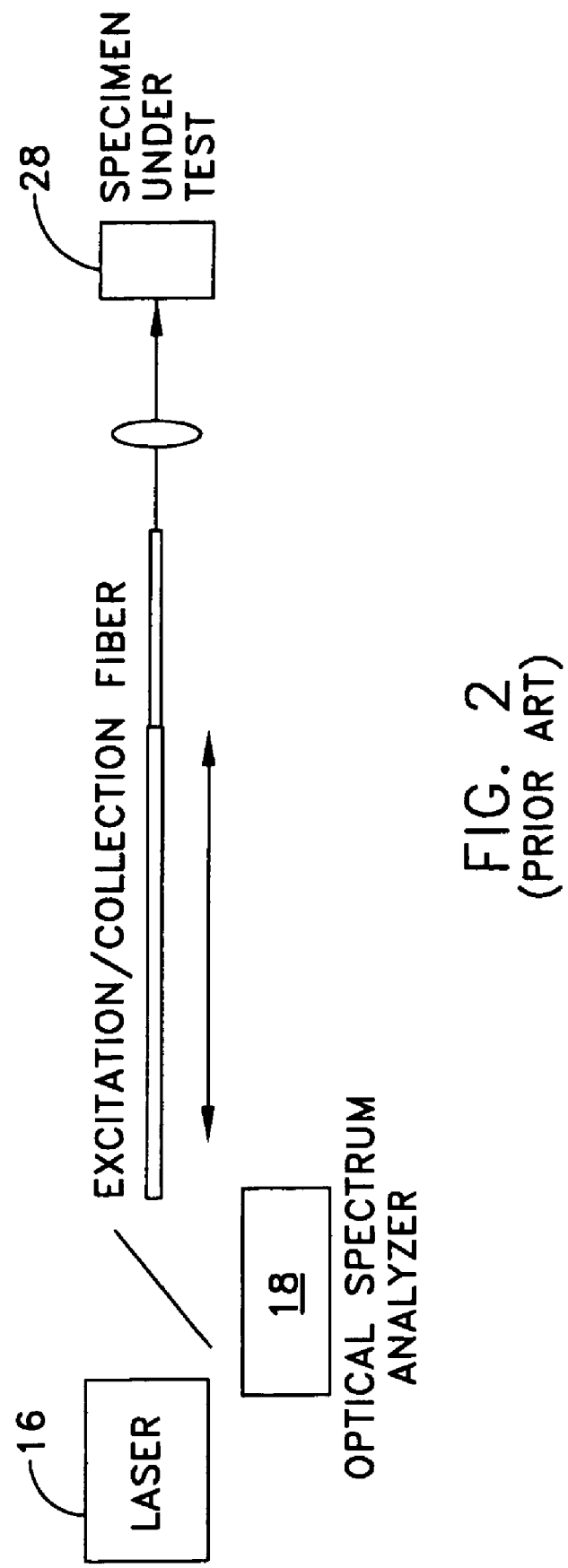
FIG. 2 is a schematic illustration of a prior art system for producing Raman signatures.

The improved Raman spectroscopy system (FIG. 5) includes an optical probe assembly 20 which comprises a dichroic beam splitter/demultiplexer 22, a single hollow-core photonic bandgap fiber/light guide 24, and a lens coupling unit 26.

The dichroic beam splitter/demultiplexer 22 is used to spatially separate the reflected lasing signal from the specimen's Raman signature.

The photonic bandgap fiber/light guide 24 allows the copropagation of the high intensity laser light with the Stokes shifted Raman signature from a specimen 28, while introducing little background Raman onto the collected signature. This fiber/light guide 24 can be placed in a ruggedized sheath 30 for environmental protection. The photonic bandgap fiber/light guide 24 exhibits a low Raman cross section inasmuch as a large fraction of the optical power is located in the air filled hollow core 32 or in air filled holes of the fiber cladding (not shown). The core 32 preferably is encased in a glass cladding 34.

The lens coupling unit 26 allows for efficient excitation and collection from the specimen 28.

Raman spectroscopy thus works by launching from the laser source 16 (FIG. 5) laser light of a selected wavelength, typically in the visible or near infrared, at the specimen 28 and collecting to the optical spectrum analyzer 18 light which has been Stokes shifted to longer wavelengths through vibrational mode interactions. By studying the position in energy of these shifted peaks, a signature of a particular material is obtained.

The practical need to hold the specimen 28 typically introduces amorphous glass or another material into the optical path very near the specimen under test and within a collection numerical aperture (NA). The amorphous glass or other material may crate an inherent Raman signature which may interfere with the Raman signature of specimen 28. The amorphous nature of the glass 36 (FIG. 7) causes the broad Raman peak 38 (shown in FIG. 3) which is collected and superimposed onto the Raman signature of the specimen. The result is a decrease in sensitivity and, hence, material selectivity. The dashed line 38 indicates the background from the sample vial's photon-phonon interactions in a Raman signature. It is seen that the dashed line obscures the detection of some of the weaker intensity peaks within the specimen's Raman signature.

Figure 7:
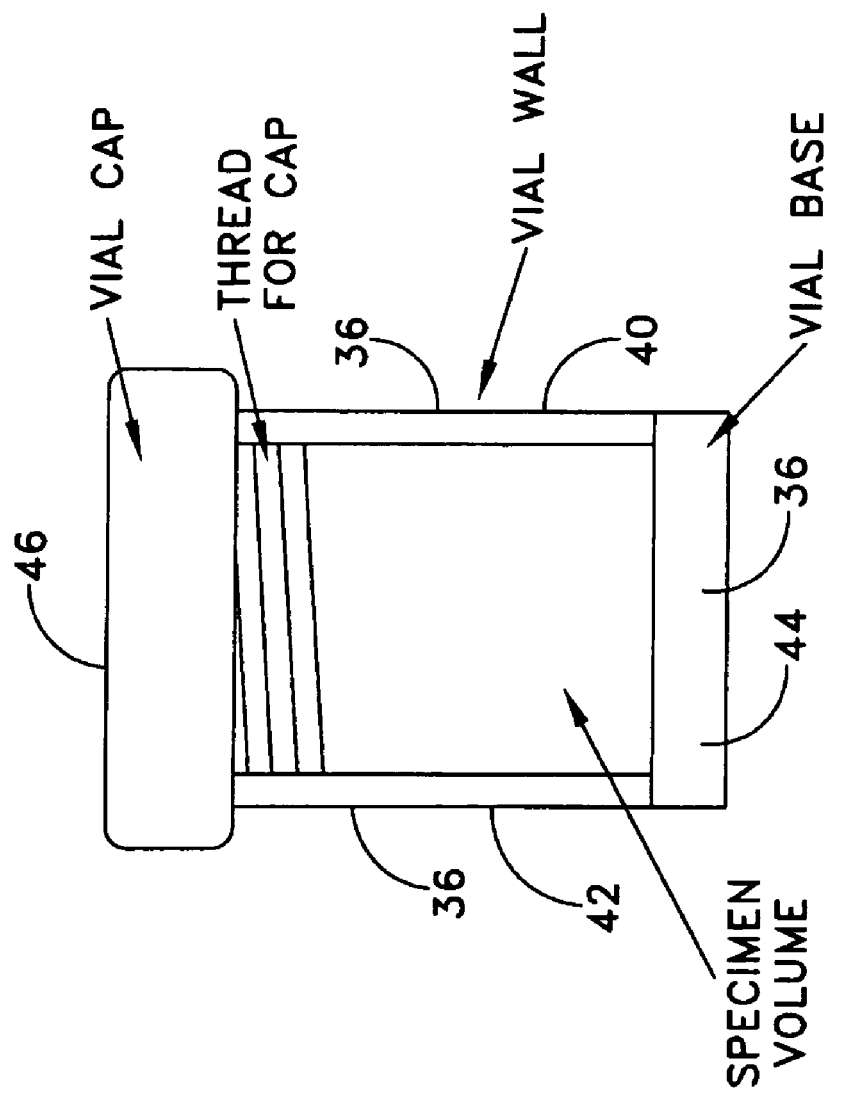
FIG. 7 is a side elevational view of a prior art specimen holder for a spectroscopy system.
Figure 8:
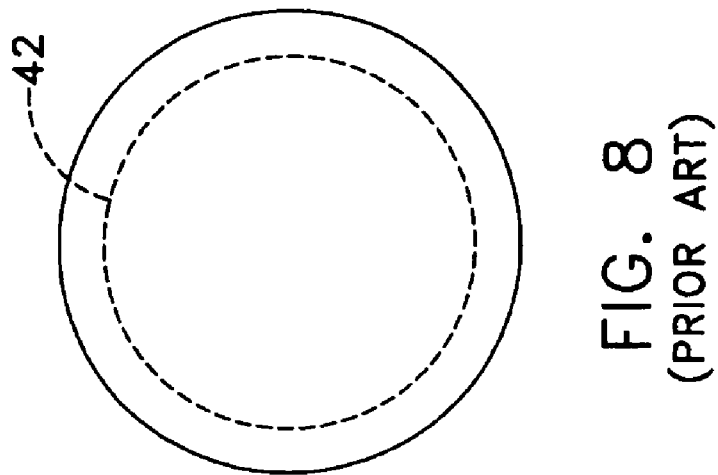
FIG. 8 is a top view of the holder of FIG. 7.

FIGS. 7 and 8 illustrate a conventional amorphous glass specimen vial 40 used in many biological applications. Typical dimensions are ~0.5"×~0.5"×~1", cylindrical, as shown, or rectangular.

Figure 3:
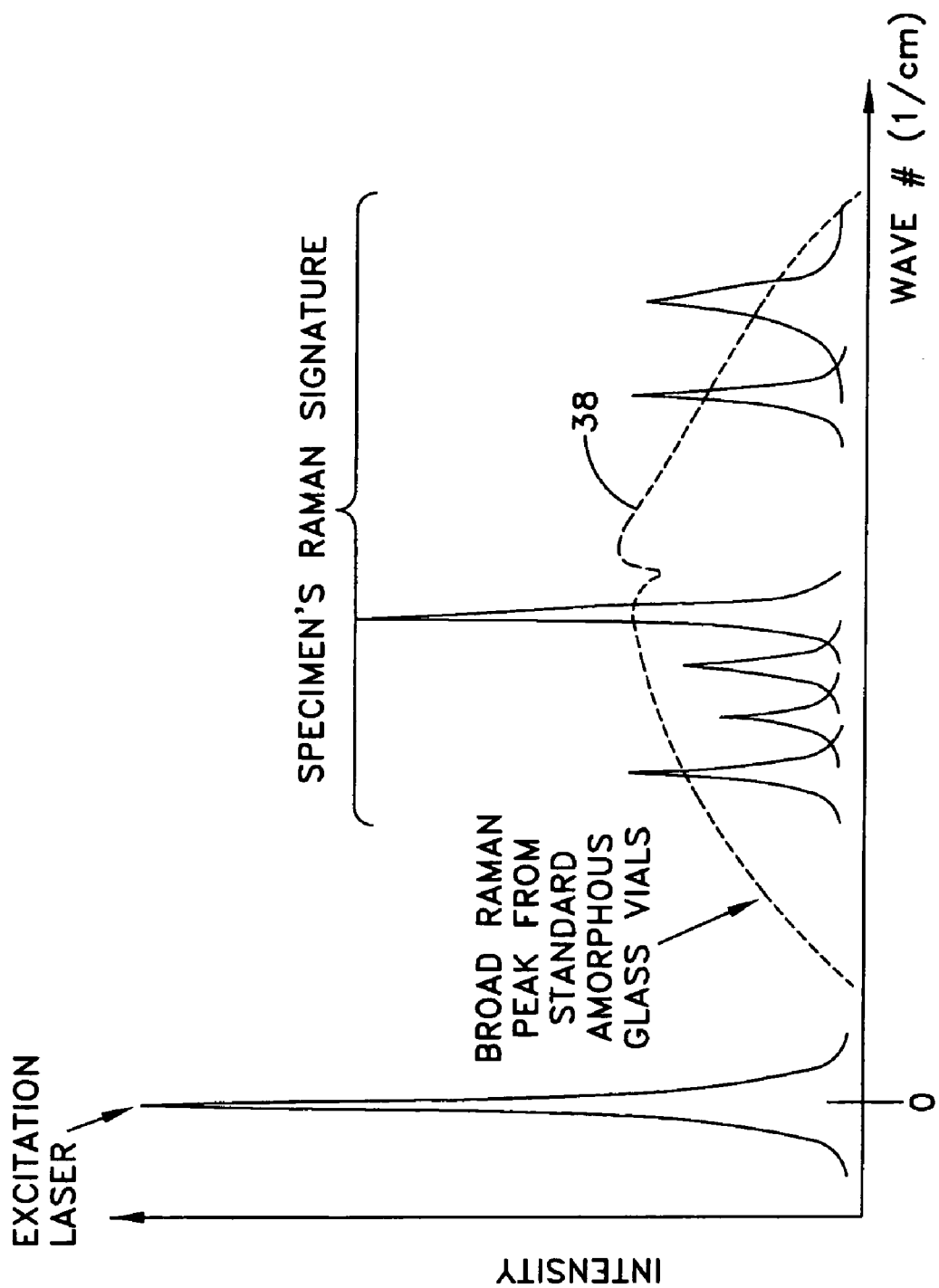
FIG. 3 is a representation of a prior art optical spectrum analyzer display of a Raman signature.

It is extremely desirable to eliminate the broad (dashed-line) peak in the Raman spectrum shown in FIG. 3. It is also greatly beneficial to narrow the Raman signature of the specimen vial 40, so fewer Raman peaks of the specimen are obscured within the spectrum. Positioning this narrower spectrum outside the spectral region of interest further increases material identification selectivity. This can be accomplished through the use of a specimen vial in which at least a portion of one or more of the walls 42, base 44, or lid 46 is made from single crystalline material.

Figure 9:
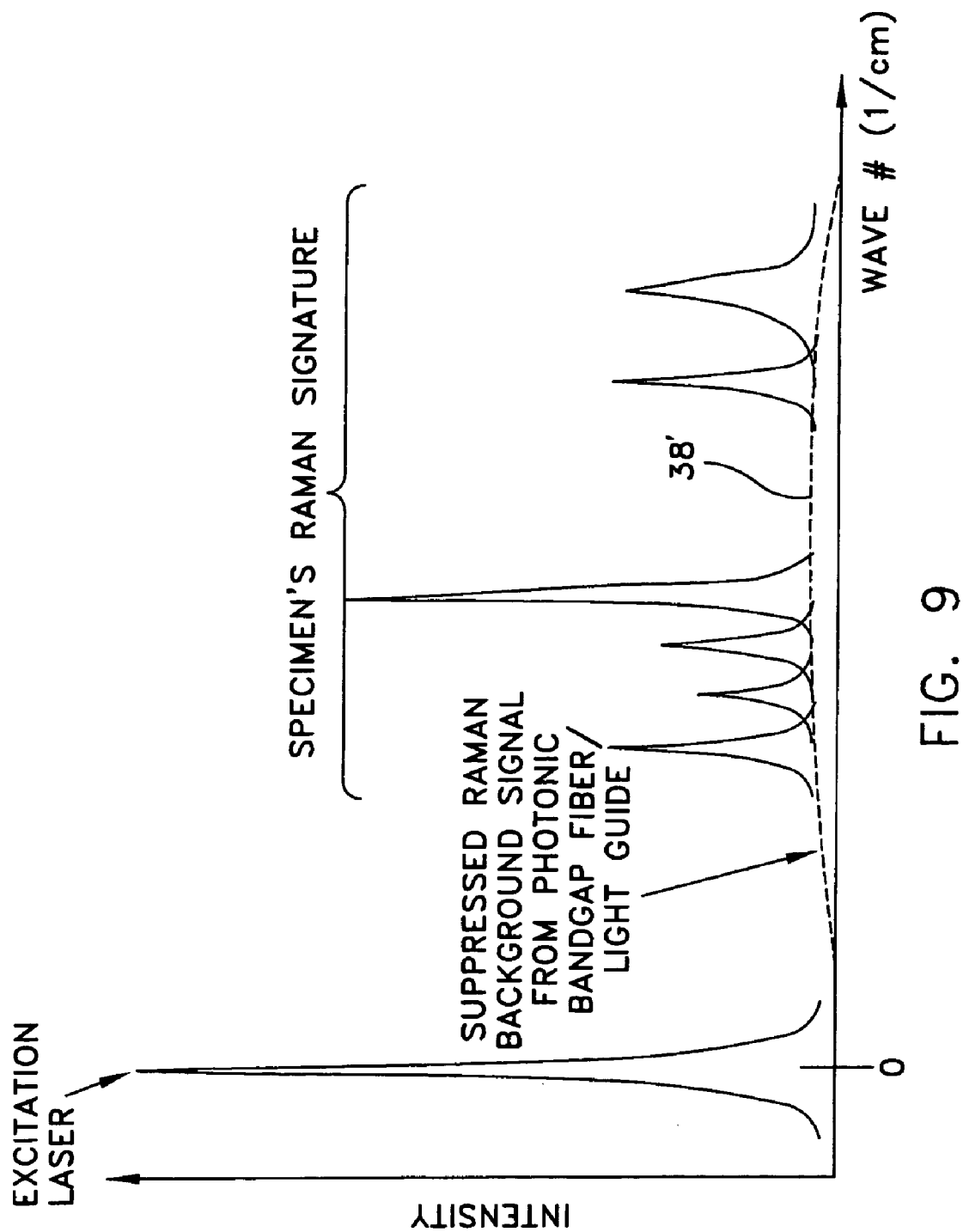
FIG. 9 is an optical spectrum analyzer display of a Raman signature utilizing a new specimen holder.

An appropriate single crystalline material is selected based upon its Stokes shift relative to the specimen of interest, the narrowness of its Raman signature, the through-loss to the excitation and shifted wavelengths, and ease of fabrication into a vial. Examples of such single crystalline materials for this application include Sapphire, Single-Crystalline Quartz, GaN, $CaF_2$, Silicon, GaAs, and InP. FIG. 9 illustrates the Raman signature from a single crystalline sample vial, and shows the reduced broad peak 38'.

Figure 10:
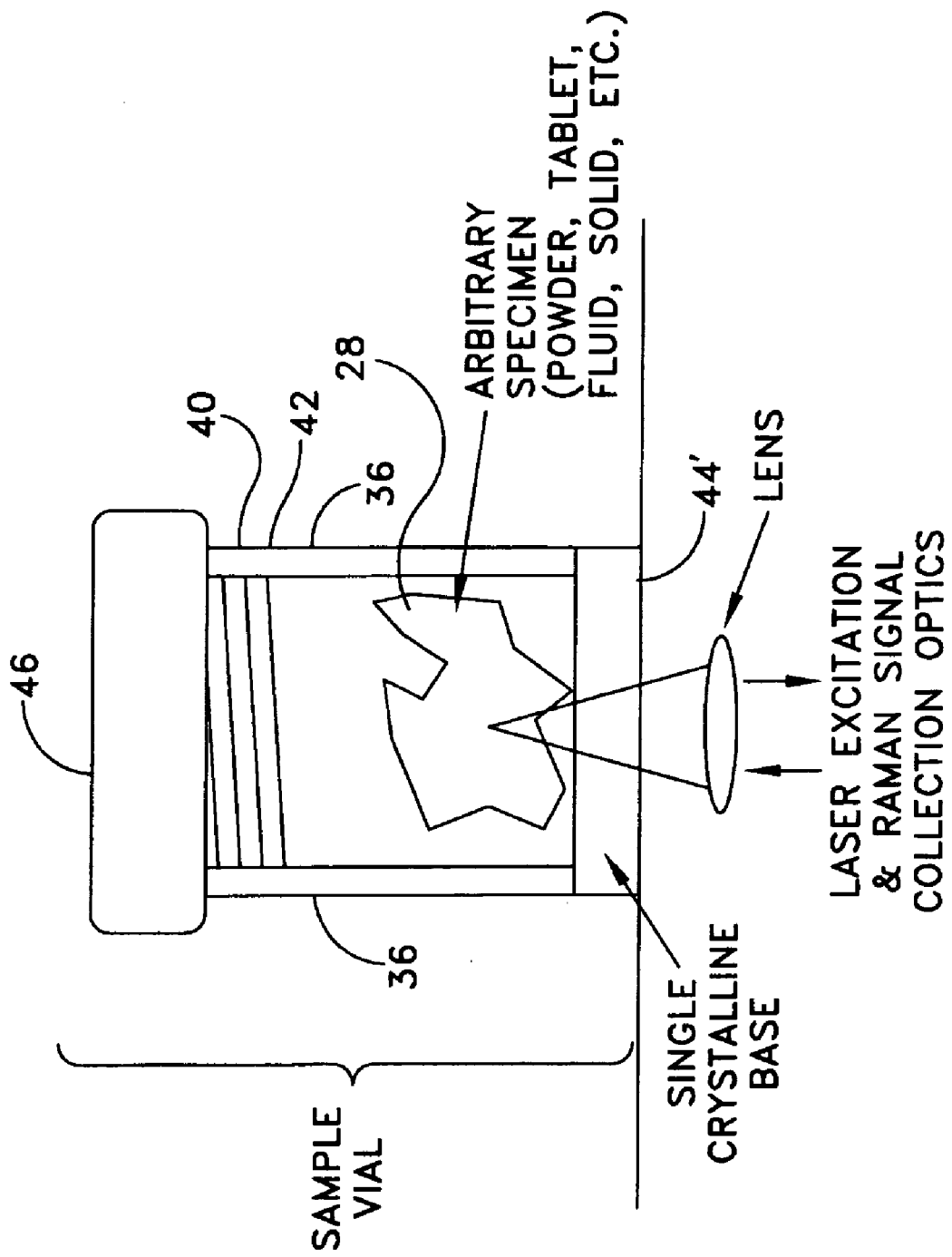
FIG. 10 is a diagrammatic side elevational view of the new specimen holder and a proximate lens of an associated spectroscopy system.

Due to the sharp and well defined spectral position and shape of the Raman signature of single crystalline material, this peak is useful as a calibration reference for the accompanying spectrometer system. The spectral transfer function can as a result be continuously monitored and deconvolved. In view of cost considerations, the entire specimen vial 40 need not be of single crystalline material. If excitation of the specimen and collection of the Raman signature is conducted through the bottom of the vial, as shown in FIG. 10, only a portion of the base 44' of the specimen holder 40 needs to be of the crystalline material.

Such a vial can be made through fabricating the walls 42 and threads 48 as a tube, using conventional glass manufacturing techniques. The single crystalline base 44' can then be attached and sealed to the walls 42 with low melting temperature glass.

Figure 4:
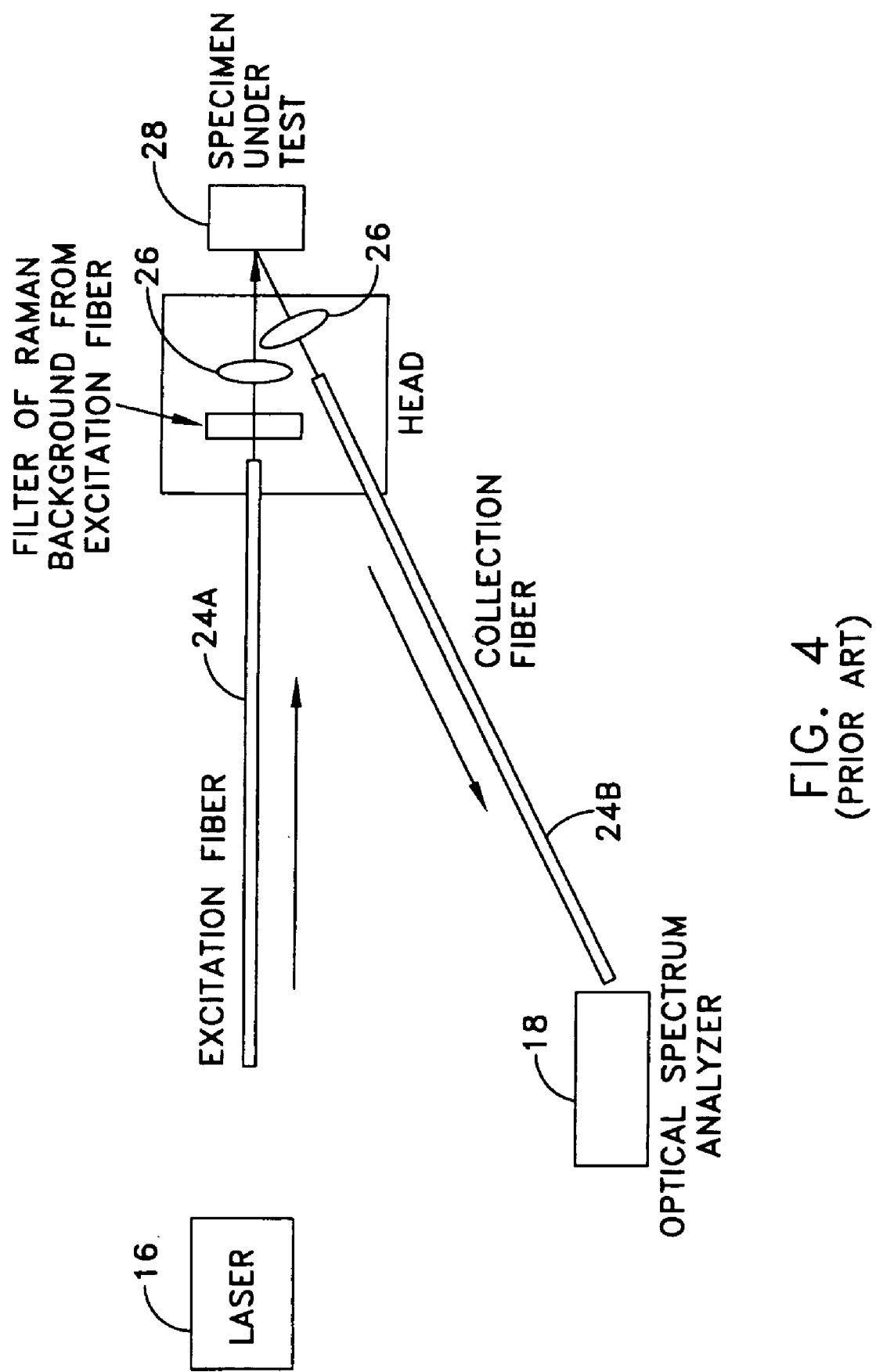
FIG. 4 is a diagrammatic illustration of a prior art Raman spectroscopy system featuring two optical fibers including an excitation fiber and a collection fiber.
Figure 11:
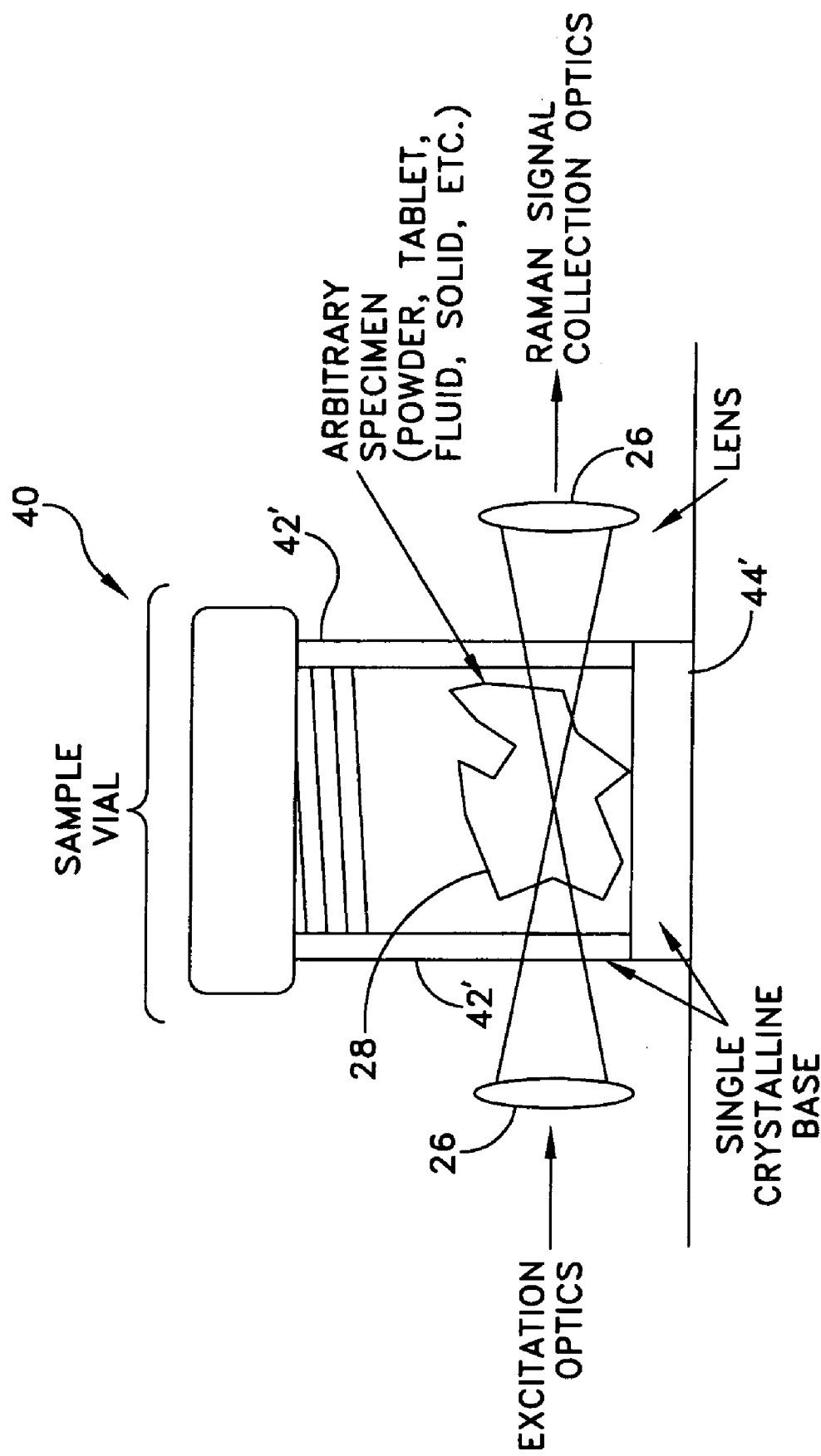
FIG. 11 is similar to FIG. 10, but illustrative of an alternative embodiment of specimen holder.

For excitation and collection through the side of the vial as shown in FIG. 11, only the walls 42' need to be made of single crystalline material. While for maximum benefit, it is desirable to use the vial 42' of FIG. 11 in conjunction with the above described improved optical probe assembly 20 having a single fiber light guide 24 (FIGS. 5 and 6), the vial 42' may also be used in conjunction with any Raman spectroscopy system including the aforementioned prior art Raman spectroscopy system, illustrated in FIG. 4, with the provision of a lens 26 on either side of the vial, as depicted in FIG. 11.

Figure 12:
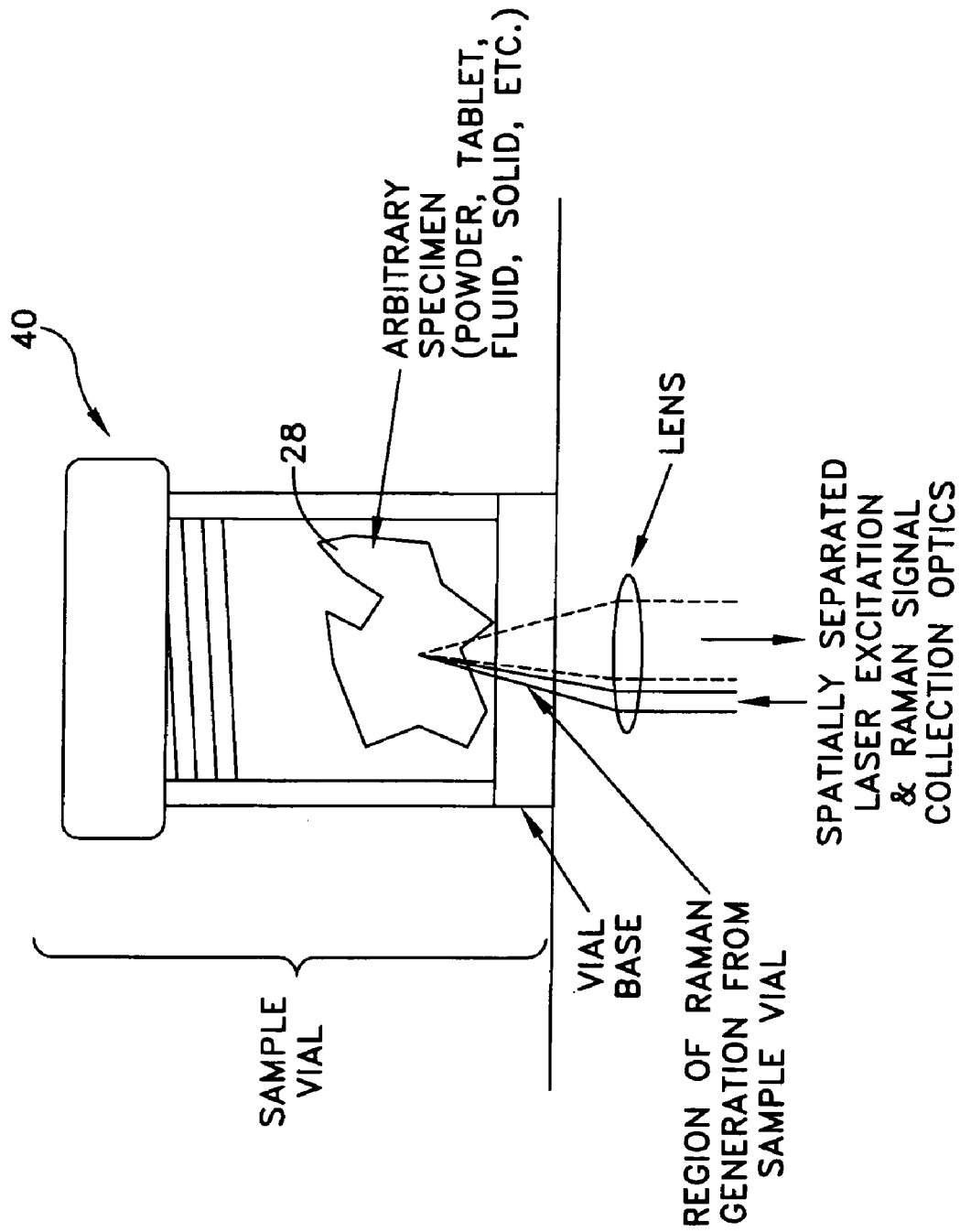
FIG. 12 is similar to FIG. 10, but illustrative of a further alternative embodiment of specimen holder and associated spectroscopy system lens.

To further reduce the impact of the Raman signature of the material of a sample vial on the specimen's signature, a spatially separated geometry of optical collection can be used. This material includes, for example, amorphous glass and crystalline material. FIG. 12 illustrates this method of collection. The Raman signature from the sample vial due to the high-power excitation laser is spatially positioned to be outside the NA of the collection path. This geometrical overlap reduction is used to further reduce and eliminate the detrimental effect on the specimen's identification and selectivity.

There is thus provided a Raman spectroscopy system and method including an optical probe assembly which exhibits a low Raman cross section and which reduces background signal contamination of the Raman signature of a specimen, the optical probe being of a compact, flexible and rugged structure.

There is further provided a specimen holder, or vial, which eliminates the problems inherent in the use of specimen holders having walls of a material, such as amorphous glass, which interfere with Raman spectroscopy.

It will be understood that many additional changes in the details, materials, steps and arrangements of parts, which have been herein described and illustrated in order to explain the nature of the invention, may be made by those skilled in the art within the principles and scope of the invention as expressed in the appended claims.

What is claimed is:

1. A Raman spectroscopy system comprising:
    a laser source for providing a laser beam;
    an optical probe assembly comprising:
        a photonic crystal light guide for receiving the laser beam from said laser source and for directing the laser beam toward a specimen of selected material;
        a lens for receiving the laser beam in said light guide and directing the beam onto the specimen, and for receiving reflected light from the specimen and directing the reflected light back through said light guide; and
        a dichroic beam splitter for directing a portion of the reflected beam out of said optical probe assembly; and
    an optical spectrum analyzer for receiving the portion of the reflected beam and for exhibiting a Raman signature of the specimen.

2. The system in accordance with claim 1 wherein said light guide comprises no more than one hollow photonic bandgap fiber waveguide.

3. The system in accordance with claim 2 wherein said light guide comprises glass cladding.

4. The system in accordance with claim 3 wherein said light guide further comprises a flexible protective sheath disposed around the light guide.

5. The system in accordance with claim 2 wherein said hollow photonic fiber is filled with gas.

6. The system in accordance with claim 5 wherein said gas is air.

7. The system in accordance with claim 5 wherein said gas comprises a known Raman signature, and wherein the Raman signature of the gas is used to calibrate said spectrum analyzer.

8. The system in accordance with claim 5 wherein the specimen is a gas, and wherein said gas of said photonic fiber is configured to increase interaction length of the gas the specimen.

9. The system in accordance with claim 1 wherein the portion of the reflected beam comprises the Raman signature portion of the beam and said beam splitter is adapted to spatially separate the Raman signature of the specimen from the reflected beam and to direct the portion of the reflected beam to said optical specimen analyzer.

10. The system in accordance with claim 1 further comprising a holder for the specimen.

11. The system in accordance with claim 10 wherein said holder comprises a vial having a top member, a bottom member, and a side wall member, and further wherein at least one of said top member, said bottom member, and said side wall member comprises a single crystalline material.

12. The system in accordance with claim 11 wherein the single crystalline material comprises a material selected from a group of materials consisting of Sapphire, Quartz, GaN, $CaF_2$, Silicon, GaAs, and InP.

13. The system in accordance with claim 11 wherein said bottom member comprises the single crystalline material, and wherein said lens is disposed proximate said bottom member.

14. The system in accordance with claim 13 wherein the laser beam from said laser source passes through a first portion of said lens, the reflected light from said specimen passes through a second portion of said lens, and said first portion and said second portion are at off-set spatial locations from each other.

15. The system in accordance with claim 11 wherein said side wall member comprises the single crystalline material.

16. A holder for a specimen of material for which a Raman signature is to be generated, the holder comprising:
    a vial having a top member, a bottom member, and a wall member,
    wherein one of the top member, the bottom member, and the wall member comprises a single crystalline material, and the others of the top member, the bottom member and the wall member are formed out of a different material.

17. The holder in accordance with claim 16 wherein the single crystalline material comprises a material selected from a group of materials consisting of Sapphire, Quartz, GaN, $CaF_2$, Silicon, GaAs, and InP.

18. The holder in accordance with claim 16 wherein said bottom member comprises the single crystalline material, said wall member comprises amorphous glass, and said bottom member is joined to the wall member by melted amorphous glass.

19. A method for producing a Raman signature display, the method comprising the steps of:
    operating a laser source to produce a laser beam;
    directing the laser beam through a crystalline light guide from a first end thereof to a second end thereof and through a lens associated with the crystalline light guide;
    directing the laser beam further onto a selected specimen from which light projected thereonto is reflected back to the lens associated with the crystalline light guide;
    passing the reflected light back through the crystalline light guide from the second end thereof to the first end thereof;
    dividing the reflected light at the first end of the crystalline light guide into a Raman signature portion and a second portion comprising a remainder of the reflected light;
    directing the signature portion of the reflected light to an optical spectrum analyzer; and
    operating the analyzer to provide a signature display.

20. A method for producing a Raman signature display, the method comprising the steps of:
    placing a specimen for which a Raman signature is desired in a holder having at least one portion of one wall of a single crystalline material;
    operating a laser source to produce a laser beam;
    directing the laser beam through a light guide and through a lens associated with the light guide;
    directing the laser beam through the at least one portion of one wall of the holder and onto the specimen from which light projected thereonto is reflected back though a light guide into an optical spectrum analyzer; and
    operating the analyzer to provide a signature display.

21. A Raman spectroscopy optical probe assembly comprising:

a photonic crystal light guide for receiving a laser beam from a laser source and for directing the laser beam toward a specimen of selected material; and a lens for receiving the laser beam in said light guide and directing the beam onto the specimen, and for receiving reflected light from the specimen and directing the reflected light back through said fiber light guide.

* * * * *